US008551972B2

(12) United States Patent
Kranenburg et al.

(10) Patent No.: US 8,551,972 B2
(45) Date of Patent: Oct. 8, 2013

(54) AGONISTS OF $A_{2A}$ ADENOSINE RECEPTORS FOR TREATING RECURRENT TUMOR GROWTH

(75) Inventors: Onno Kranenburg, Utrecht (NL); Jarmila van der Bilt, Amsterdam (NL); Inne Borel Rinkes, Utrecht (NL); Jayson M. Rieger, Charlottesville, VA (US)

(73) Assignee: Adenosine Therapeutics, LLC, Charlottesville, VA (US)

( * ) Notice: Subject to any disclaimer, the term of this patent is extended or adjusted under 35 U.S.C. 154(b) by 31 days.

(21) Appl. No.: 12/940,457

(22) Filed: Nov. 5, 2010

(65) Prior Publication Data

US 2011/0166094 A1    Jul. 7, 2011

Related U.S. Application Data

(63) Continuation of application No. 12/102,185, filed on Apr. 14, 2008, now abandoned.

(60) Provisional application No. 60/925,736, filed on Apr. 23, 2007.

(51) Int. Cl.
*A01N 43/04* (2006.01)
*A01N 43/00* (2006.01)
*A61K 31/70* (2006.01)
*A61K 31/33* (2006.01)

(52) U.S. Cl.
USPC ............................................. 514/46; 514/183

(58) Field of Classification Search
None
See application file for complete search history.

(56) References Cited

U.S. PATENT DOCUMENTS

2005/0220799 A1* 10/2005 Sitkovsky et al. ......... 424/184.1
2007/0207979 A1* 9/2007 Podhajsky ..................... 514/47

* cited by examiner

*Primary Examiner* — Anna Pagonakis
(74) *Attorney, Agent, or Firm* — Vance Intellectual Property PC

(57) ABSTRACT

The present invention relates to a method for treating recurrent tumor metastases following liver resection that includes administration of an effective amount of an agonist of $A_{2A}$ adenosine receptors (ARs).

Figure 1:
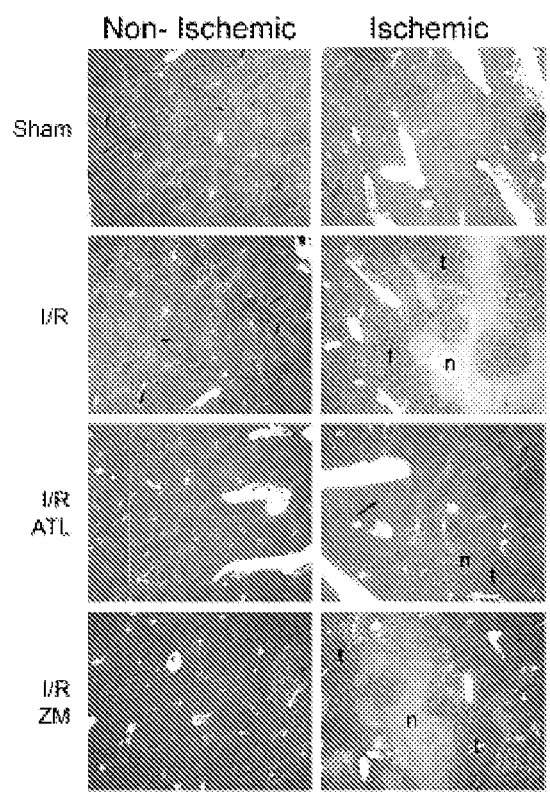

7 Claims, 3 Drawing Sheets

AGONISTS OF $A_{2A}$ ADENOSINE RECEPTORS FOR TREATING RECURRENT TUMOR GROWTH

RELATED APPLICATIONS

The present application is a continuation of "Agonists of A2A Adenosine Receptors For Treating Recurrent Tumor Growth in the Liver Following Resection," U.S. application Ser. No. 12/102,185 filed Apr. 14, 2008, which claims priority to U.S. Provisional Application No. 60/925,736, filed Apr. 23, 2007, each of which are expressly incorporated herein by reference.

FIELD OF THE INVENTION

The present invention relates to a method for treating recurrent tumor metastases following liver resection that includes administration of an effective amount of an agonist of $A_{2A}$ adenosine receptors (ARs).

BACKGROUND OF THE INVENTION

In the United States, approximately 150,000 patients are diagnosed with colorectal cancer each year. About 20% of these patients have metastatic deposits of colorectal cancer in the liver only at the time of diagnosis or develop such metastases during the course of their illness. In the absence of treatment, the prognosis for patients with hepatic colorectal metastases is dismal, with 5-year survival rates of 3% or less. There is now evidence that resection of such metastases can improve the prognosis. Although liver resection is not the primary treatment for most patients with hepatic colorectal metastases, appropriate liver resection is the standard of care for treatment of patients with isolated hepatic colorectal metastases. The majority of patients experience recurrence following hepatic resection of colorectal metastases. Patients at high risk for recurrence after hepatic resection are those who present with multiple hepatic metastases (vs. single metastases), large metastatic tumors (>5 cm), a high CEA serum concentration (>200 ng/mL), a node-positive primary colorectal cancer, or synchronous tumors (primary colorectal cancer and hepatic colorectal metastases). A treatment that reduced or eliminated recurrence after hepatic resection would be highly desirable.

The notion that tissue inflammation and tumor growth are intricately associated phenomena is relatively old, but the cell types and signaling intermediates that define this interrelationship are only beginning to be identified, as are the potential targets for therapeutic intervention. Most studies have focused on elucidating how chronic inflammation promotes the progression of pre-malignant to malignant lesions. Previous work has shown that the outgrowth of late stage tumors (colorectal liver metastases) is stimulated by inflammation and necrosis of liver tissue following ischemia/reperfusion (I/R)(see Hepatology 2005, 42, 165-175; and, Br. J. Surg. 2006, 93, 1015-1022). Unfortunately, the mechanisms underlying the accelerated outgrowth of inflammation-associated late-stage metastatic tumors are unknown. Thus, the development of an effective treatment that suppresses surgery-induced inflammation-associated tumor growth is desirable.

SUMMARY OF THE INVENTION

The present invention provides a novel method for treating recurrent tumor metastases following liver resection comprising administering to a patient in need thereof a therapeutically effective amount of an $A_{2A}$ adenosine receptor agonist or a pharmaceutically acceptable salt thereof.

The present invention also provides pharmaceutical compositions comprising an $A_{2A}$ receptor agonist or a pharmaceutically acceptable salt thereof effective to treat recurrent tumor metastases following liver resection and a pharmaceutically acceptable excipient.

The present invention provides a compound of the present invention or a pharmaceutically acceptable salt thereof for use in medical therapy.

The present invention also provides the use of a compound of the present invention or a pharmaceutically acceptable salt thereof for the manufacture of a medicament for the treatment of recurrent tumor metastases following liver resection.

These and other objects, which will become apparent during the following detailed description, have been achieved by the inventors' discovery that an agonist of an $A_{2A}$ receptor can be used to treat recurrent tumor metastases following liver resection.

BRIEF DESCRIPTION IF THE DRAWINGS

The accompanying drawings, which are incorporated herein and form a part of the specification, illustrate some aspects of the present invention and together with the description, serve to explain the principles of the invention.

FIG. 1. Micrometasases were induced as described in paragraph 00242. Mice were subjected to left lobar I/R and were treated with ATL313 or vehicle as described in section 00242. Five days after the operation (day 10 of the exp) the mice were sacrificed; the livers were harvested and stained using haematoxylin and eosin. Areas of normal liver tissue (dark pink), tumor tissue (t, purple) and necrosis (m, light pink) can easily be discriminated. The figure shows that ATL treatment prevents tissue necrosis and necrosis-associated tumor growth.

Figure 2:
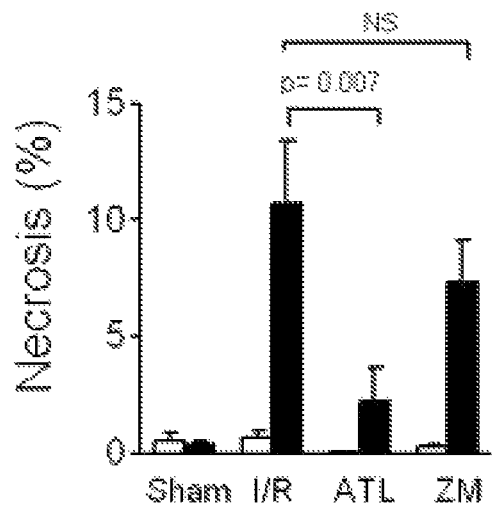

FIG. 2. This figure shows quantifications of the area of liver tissue that has been replaced by tumor tissue (Hepatic Replacement Area (HRA) in sham-operated mice, in I/R-subjected mice, and in I/R-subjected mice treated with ATL or ZM. White bars correspond to HRA values measured in the (non-clamped) right and median liver lobes. The black bars correspond to HRA values measured in the left (clamped) lobes.

Figure 3:
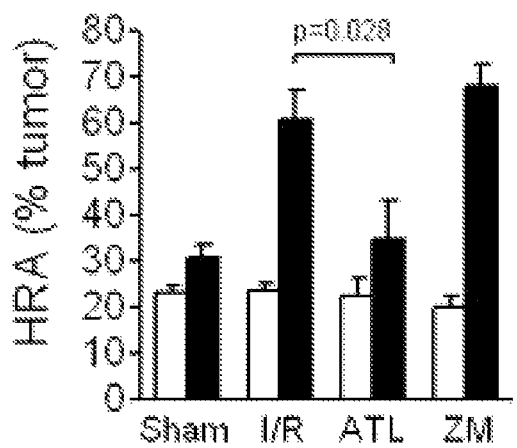

FIG. 3. This figure shows quantifications of the area of liver tissue that has been replaced by necrotic tissue in sham-operated mice, in I/R-subjected mice (left lobe), and in I/R-subjected mice treated with ATL or ZM. White bars correspond to necrosis values measured in the (non-clamped) right and median liver lobes. The black bars correspond to necrosis values measured in the left (clamped) lobes.

Figure 4:
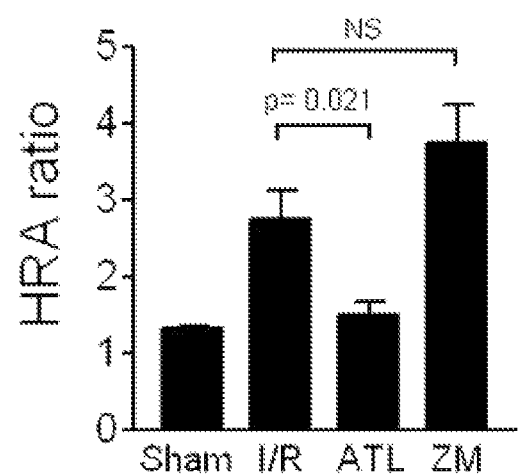

FIG. 4: This figure shows the ratio of hepatic replacement area (HRA) values in ischemic (clamped) left liver lobes versus non-ischeme right and median liver lobes. In sham-operated mice this ratio is approximately 1. The percentage tumor area in the left lobes is equal to that in the right and median lobes. However, in I/R subjected mice tumor growth in the clamped (left lobes) is approximately 2.5-fold higher than that in the non-clamped (right and median) lobes. ATL treatment prevents the increase in tumor growth in the left (clamped) liver lobes and thereby normalizes the ratio between tumor growth in the left and right/median lobes to 1. ZM, which inactivates the $A_{2A}R$, appears to aggravate tumor growth in the clamped liver lobes, thereby increasing the left-to-right/median ratio, although this difference did not reach statistical significance.

DETAILED DESCRIPTION OF THE INVENTION

A mouse model has been developed in which selective temporary occlusion of blood flow into the left liver lobe results in a profound acceleration of tumor growth in the clamped, but not in the unclamped liver lobes. Accelerated tumor growth is closely associated with tissue necrosis and inflammation. Administration of the immune suppressant ATL313, an adenosine $A_{2A}$ receptor agonist, almost completely prevented tissue necrosis, inflammation, and accelerated tumor growth following I/R (see FIG. 1). The results of these studies show that administration of an $A_{2A}$ receptor agonist (e.g., ATL-313) is efficacious in reducing tumor metastases following liver resection.

In light of this discovery, the present invention provides a novel method for treating recurrent tumor metastases following liver resection, comprising: administering to a patient in need thereof a therapeutically effective amount of an $A_{2A}$ adenosine receptor agonist. The agonist can be administered prior to resection, during resection, following resection, and a combination thereof.

Examples of agonists of $A_{2A}$ adenosine receptors that are expected to useful in the practice of the present invention include compounds having the formula I or a stereoisomer or pharmaceutically acceptable salt thereof:

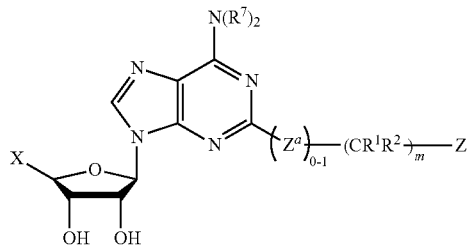

wherein
$Z^a$ is C≡C, O, NH, or NHN=$CR^{3a}$;
Z is $CR^3R^4R^5$ or $NR^4R^5$;
each $R^1$ is independently hydrogen, halo, —$OR^a$, —$SR^a$, $(C_1-C_8)$alkyl, cyano, nitro, trifluoromethyl, trifluoromethoxy, $(C_3-C_8)$cycloalkyl, heterocycle, heterocycle$(C_1-C_8)$alkylene-, aryl, aryl$(C_1-C_8)$alkylene-, heteroaryl, heteroaryl$(C_1-C_8)$alkylene-, —$CO_2R^a$, $R^aC(=O)O$—, $R^aC(=O)$—, —$OCO_2R^a$, $R^bR^cN(R^b)$—, $R^bR^cN$—, $R^bR^cNC(=O)$—, $R^aC(=O)N(R^b)$—, $R^bR^cNC$(=O)N($R^b$)—$R^bR^cNC(=S)N(R^b)$—, —$OPO_3R^a$, $R^aOC$(=S)—, $R^aC(=S)$—, —$SSR^a$, $R^aS(=O)$—, $R^aS(=O)_2$—, or —N=$NR^b$;

each $R^2$ is independently hydrogen, halo, $(C_1-C_8)$alkyl, $(C_3-C_8)$cycloalkyl, heterocycle, heterocycle$(C_1-C_8)$alkylene-, aryl, aryl$(C_1-C_8)$alkylene-, heteroaryl, or heteroaryl$(C_1-C_8)$alkylene-;

alternatively, $R^1$ and $R^2$ and the atom to which they are attached is C=O, C=S or C=$NR^d$, $R^4$ and $R^5$ are independently H or $(C_1-C_8)$alkyl;

alternatively, $R^4$ and $R^5$ together with the atom to which they are attached form a saturated, partially unsaturated, or aromatic ring that is mono-, bi- or polycyclic and has 3, 4, 5, 6, 7, 8, 9 or 10 ring atoms optionally having 1, 2, 3, or 4 heteroatoms selected from non-peroxide oxy (—O—), thio (—S—), sulfinyl (—SO—), sulfonyl (—$S(O)_2$—) or amine (—$NR^b$—) in the ring;

wherein $R^4$ and $R^5$ are independently substituted with 0-3 $R^6$ groups or any ring comprising $R^4$ and $R^5$ is substituted with from 0 to 6 $R^6$ groups;

each $R^6$ is independently hydrogen, halo, —$OR^a$, —$SR^a$, $(C_1-C_8)$alkyl, cyano, nitro, trifluoromethyl, trifluoromethoxy, $(C_1-C_8)$cycloalkyl, $(C_6-C_{12})$bicycloalkyl, heterocycle, heterocycle $(C_1-C_8)$alkylene-, aryl, aryl$(C_1-C_8)$alkylene-, heteroaryl, heteroaryl$(C_1-C_8)$alkylene-, —$CO_2R^a$, $R^aC(=O)$O—, $R^aC(=O)$—, —$OCO_2R^a$, $R^bR^cNC(=O)O$—, $R^aC(=O)N(R^b)$—, $R^bR^cN$—, $R^bR^cNC(=O)$—, $R^bR^cNC(=O)N(R^b)$—, $R^bR^cNC(=O)N(R^b)$—, $R^bR^cNC(=S)N(R^b)$—, —$OPO_3R^a$, $R^aOC(=S)$—, $R^aC(=S)$—, —$SSR^a$, $R^aS(=O)$—, —$NNR^b$, or two $R^6$ groups and the atom to which they are attached is C=O, C=S; or two $R^6$ groups together with the atom or atoms to which they are attached can form a carbocyclic or heterocyclic ring comprising from 1-6 carbon atoms and 1, 2, 3, or 4 heteroatoms selected from non-peroxide oxy (—O—), thio (—S—), sulfinyl (—SO—), sulfonyl (—$S(O)_2$—) or amine (—$NR^b$—) in the ring;

$R^3$ is hydrogen, halo, —$OR^a$, —$SR^a$, $(C_1-C_8)$alkyl, cyano, nitro, trifluoromethyl, trifluoromethoxy, $(C_3-C_8)$cycloalkyl, heterocycle, heterocycle$(C_1-C_8)$alkylene-, aryl, aryl$(C_1-C_8)$alkylene-, heteroaryl, heteroaryl$(C_1-C_8)$alkylene-, —$CO_2R^a$, $R^aC(=O)O$—, $R^aC(=O)$—, —$OCO_2R^a$, $R^bR^cNC(=O)O$—, $R^aOC(=O)N(R^b)$—, $R^bR^cN$—, $R^bR^cNC(=O)$—, $R^aC(=O)N(R^b)$—, $R^bR^cNC(=O)N(R^b)$—, $R^bR^cNC(=O)N(R^b)$—, —$OPO_3R^a$, $R^aOC(=S)$—, $R^aC(=S)$—, —$SSR^a$, $R^aS(=O)$—, $R^aS(=O)_2$—, —$NNR^b$; or if the ring formed from $CR^4R^5$ is aryl or heteroaryl or partially unsaturated then $R^3$ can be absent;

$R^{3a}$ is hydrogen, $(C_1-C_8)$alkyl, or aryl;

each $R^7$ is independently hydrogen, $(C_1-C_8)$alkyl, $(C_3-C_8)$cycloalkyl, aryl, aryl$(C_1-C_8)$alkylene, heteroaryl, or heteroaryl$(C_1-C_8)$alkylene-;

X is —$CH_2OR^a$, —$CO_2R^a$, —$CH_2OC(O)R^a$, —$C(O)NR^bR^c$, —$CH_2SR^a$, —$C(S)OR^a$, —$CH_2OC(S)R^a$, —$C(S)NR^bR^c$, or —$CH_2N(R^b)(R^c)$;

alternatively, X is an aromatic ring of the formula:

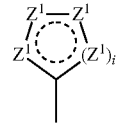

each $Z^1$ is non-peroxide oxy (—O—), $S(O)_{0-2}$, —$C(R^8)$—, or amine (—$NR^8$—), provided that at least one $Z^1$ is non-peroxide oxy (—O—), thio (—S—), sulfinyl (—SO—), sulfonyl (—$S(O)_2$—) or amine (—$NR^8$—);

each $R^8$ is independently hydrogen, $(C_1-C_8)$alkyl, $(C_1-C_8)$alkenyl, $(C_3-C_8)$cycloalkyl, $(C_3-C_8)$cycloalkyl$(C_1-C_8)$alkylene, $(C_3-C_8)$cycloalkenyl, $(C_3-C_8)$cycloalkenyl$(C_1-C_8)$alkylene, aryl, aryl$(C_1-C_8)$alkylene, heteroaryl, or heteroaryl$(C_1-C_8)$alkylene, wherein any of the alkyl or alkenyl groups of $R^8$ are optionally interrupted by —O—, —S—, or —$N(R^a)$—;

wherein any of the alkyl, cycloalkyl, heterocycle, aryl, or heteroaryl, groups of $R^1$, $R^2$, $R^3$, $R^{3a}$, $R^6$, $R^7$ and $R^8$ is optionally substituted on carbon with one or more (e.g. 1, 2, 3, or 4) substituents selected from the group consisting of halo, —$OR^a$, —$SR^a$, $(C_1-C_8)$alkyl, cyano, nitro, trifluoromethyl, trifluoromethoxy, $(C_3-C_8)$cycloalkyl, $(C_6-C_{12})$bicycloalkyl, heterocycle, heterocycle$(C_1-C_8)$alkylene-, aryl, aryloxy, aryl$(C_1-C_8)$alkylene-, heteroaryl, heteroaryl$(C_1-C_8)$alkylene-, —$CO_2R^a$, $R^aC(=O)O$—, $R^aC(=O)$—, —$OCO_2R^a$, $R^bR^cNC(=O)O$—, $R^aOC(=O)N(R^b)$—, $R^bR^cN$—, $R^bR^cNC(=O)$—, $R^aC(=O)N(R^b)$—, $R^bR^cNC(=O)N(R^b)$—, $R^bR^cNC(=S)N(R^b)$—, —$OPO_3R^a$, $R^aOC(=S)$—, $R^aC(=S)$—, —$SSR^a$, $R^aS(=O)_p$—, $R^bR^cNS(O)_p$—, and —N=$NR^b$;

wherein any $(C_1-C_8)$alkyl, $(C_3-C_8)$cycloalkyl, $(C_6-C_{12})$bicycloalkyl, $(C_1-C_8)$alkoxy, $(C_1-C_8)$alkanoyl, $(C_1-C_8)$alkylene, or heterocycle, is optionally partially unsaturated;

each $R^a$, $R^b$ and $R^c$ is independently hydrogen, $(C_1-C_{12})$ alkyl, $(C_1-C_8)$alkoxy, $(C_1-C_8)$alkoxy-$(C_1-C_{12})$alkylene, $(C_3-C_8)$cycloalkyl, $(C_3-C_8)$cycloalkyl-$(C_1-C_{12})$alkylene, $(C_1-C_8)$alkylthio, amino acid, aryl, aryl$(C_1-C_8)$alkylene, heterocycle, heterocycle-$(C_1-C_8)$alkylene, heteroaryl, or heteroaryl$(C_1-C_8)$alkylene;

alternatively $R^b$ and $R^c$, together with the nitrogen to which they are attached, form a pyrrolidino, piperidino, morpholino, or thiomorpholino ring;

wherein any of the alkyl, cycloalkyl, heterocycle, aryl, or heteroaryl groups of $R^a$, $R^b$ and $R^c$ is optionally substituted on carbon with 1 or 2 substituents selected from the group consisting of halo, $-(CH_2)_aOR^e$, $-(CH_2)_aSR^e$, $(C_1-C_8)$alkyl, $(CH_2)_aCN$, $(CH_2)_aNO_2$, trifluoromethyl, trifluoromethoxy, $-(CH_2)_aCO_2R^3$, $(CH_2)_aNR^eR^e$, and $(CH_2)_aC(O)NR^eR^e$;

$R^d$ is hydrogen or $(C_1-C_6)$alkyl;

$R^e$ is independently selected from H and $(C_1-C_6)$alkyl;

a is 0, 1, or 2;

i is 1 or 2 m is 0 to 8; and p is 0 to 2;

provided that m is at least 1 when Z is $NR^4R^5$; or a pharmaceutically acceptable salt thereof.

Specific values listed below for radicals, substituents, and ranges, are for illustration only; they do not exclude other defined values or other values within defined ranges for the radicals and substituents.

For example, specific values include compounds having the formula (Ia):

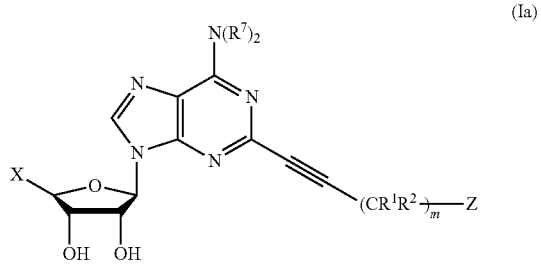

(Ia)

wherein $R^1$ is hydrogen, —OH, —$CH_2OH$, —OMe, —OAc, —$NH_2$, —NHMe, —$NMe_2$ or —NHAc;

$R^2$ is hydrogen, $(C_1-C_8)$alkyl, cyclopropyl, cyclohexyl or benzyl;

$R^3$ is hydrogen, OH, OMe, OAc, $NH_2$, NHMe, $NMe_2$ or NHAc;

$CR^4R^5$ or $NR^4R^5$ is optionally substituted with 0-2 $R^6$ groups and is cyclopentane, cyclohexane, piperidine, dihydro-pyridine, tetrahydro-pyridine, pyridine, piperazine, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, and. pyrazolidine;

alternatively, the ring $CR^4R^5$ or $NR^4R^5$ is optionally substituted with 0-4 (e.g., 0 to 2) $R^6$ groups and is selected from the group consisting of:

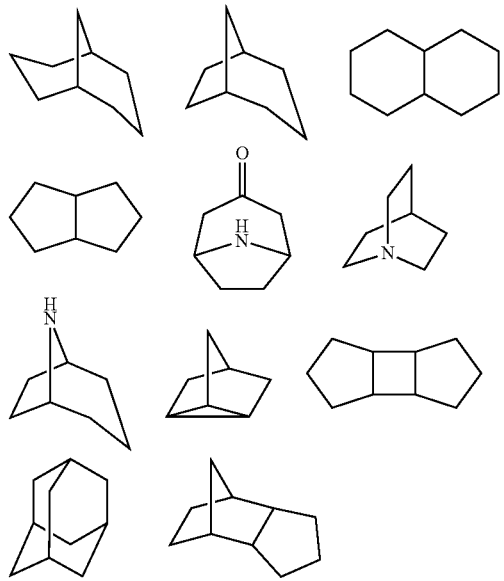

$R^6$ is hydrogen, $(C_1-C_8)$alkyl, —$OR^a$, —$CO_2R^a$, $R^aC(=O)-$, $R^aC(=O)O-$, $R^bR^cN-$, $R^bR^cNC(=O)-$, or aryl;

$R^a$, $R^b$ and $R^c$ are independently hydrogen, $(C_3-C_4)$-cycloalkyl, $(C_1-C_8)$alkyl, aryl or aryl$(C_1-C_8)$alkylene;

each $R^7$ is independently hydrogen, alkyl (e.g., $C_1-C_8$alkyl), aryl, aryl$(C_1-C_8)$alkylene or heteroaryl$(C_1-C_8)$ alkylene;

$R^8$ is methyl, ethyl, propyl, 2-propenyl, cyclopropyl, cyclobutyl, cyclopropylmethyl, —$(CH_2)_2CO_2CH_3$, or —$(CH_2)_{2-3}OH$;

X is —$CH_2OR^a$, —$CO_2R^a$, —$CH_2OC(O)R^a$, or —$C(O)NR^bR^c$;

alternatively X is selected from:

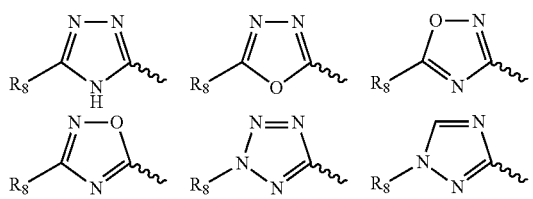

and m is 0, 1 or 2;

or a pharmaceutically acceptable salt thereof.

Additional specific values include compounds having the formula (Ia), wherein:

$R^1$ is hydrogen, OH, OMe, or $NH_2$;

$R^2$ is hydrogen, methyl, ethyl or propyl;

$R^3$ is hydrogen, OH, OMe, or $NH_2$;

the ring $CR^4R^5$ or $NR^4R^5$ is selected from the group consisting of:

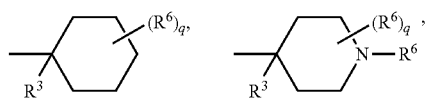

-continued

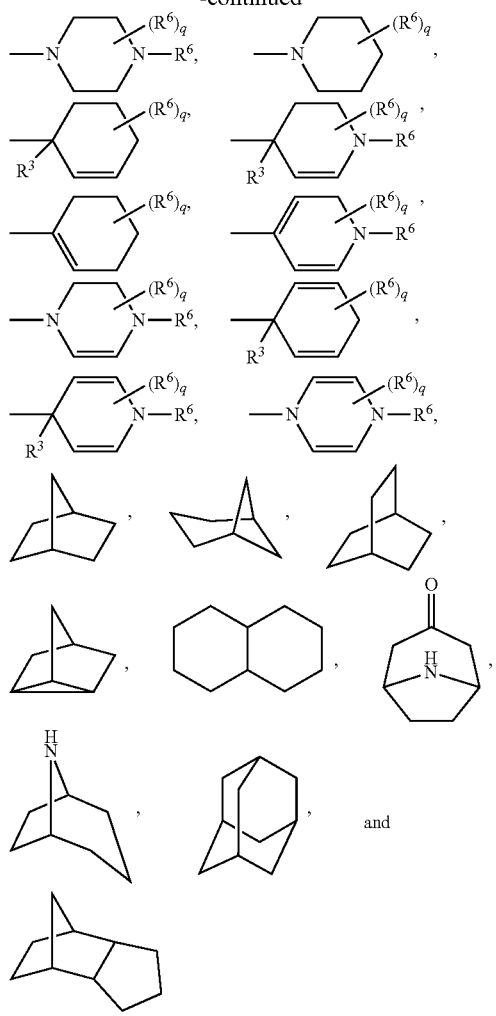

where q is from 0 to 4 (e.g., 0-2);
$R^6$ is hydrogen, $(C_1-C_8)$alkyl, —$OR^a$, —$CO_2R^a$, $R^aC(=O)$—, $R^aC(=O)O$—, $R^bR^cN$—, $R^bR^cNC(=O)$—, or aryl;
$R^a$ and $R^b$ are independently hydrogen, methyl, ethyl, propyl, butyl, ethylhexyl, cyclopropyl, cyclobutyl, phenyl or benzyl;
$N(R^7)_2$ is amino, methylamino, dimethylamino; ethylamino; pentylamino, diphenylethylamino, (pyridinylmethyl)amino, (pyridinyl)(methyl)amino, diethylamino or benzylamino; and,
$R^8$ is methyl, ethyl, propyl, or cyclopropyl;
X is —$CH_2OR^a$ or —$C(O)NR^bR^c$;
alternatively, X is selected from:

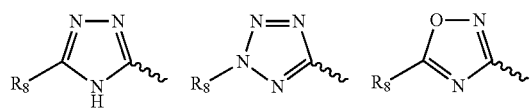

or a pharmaceutically acceptable salt thereof.
Additional specific values include compounds having the formula (Ia), wherein:
$R^1$ is hydrogen, OH, or $NH_2$;
$R^2$ is hydrogen or methyl;
$R^3$ is hydrogen, OH, or $NH_2$;
the ring $CR^4R^5$ or $NR^4R^5$ is selected from the group consisting of:

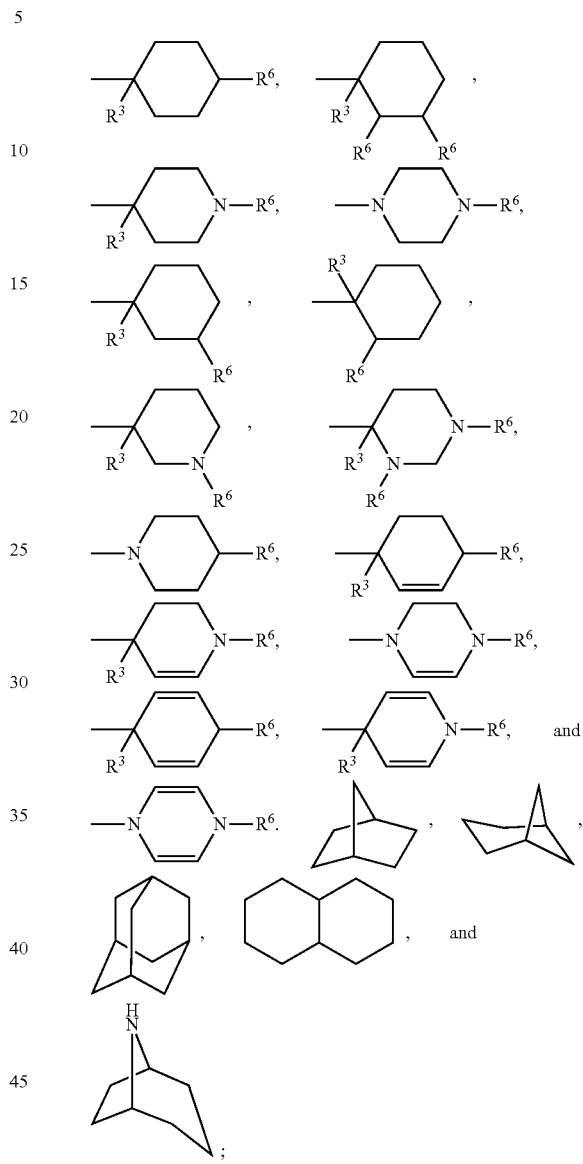

where q is from 0 to 2;
$R^6$ is hydrogen, methyl, ethyl, t-butyl, phenyl, —$CO_2R^a$ —$CONR^bR^c$, or $R^aC(=O)$—;
$R^b$ is H;
$R^a$ is methyl, ethyl, propyl, butyl, pentyl, ethylhexyl cyclopropyl, and cyclobutyl;
—$N(R^7)_2$ is amino, methylamino, dimethylamino; ethylamino; diethylamino or benzylamino;
or a pharmaceutically acceptable salt thereof.
Additional specific values include compounds having the formula (Ia), wherein:
$R^1$ is hydrogen or OH;
$R^2$ is hydrogen;
$R^3$ is hydrogen or OH;

the ring $CR^4R^5$ or $NR^4R^5$ is selected from the group consisting of:

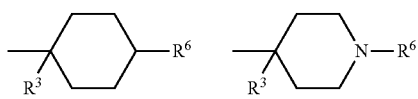

$R^6$ is hydrogen, methyl, ethyl, —$CO_2R^a$, and —$CONR^b R^c$;

$R^b$ is H;

$R^a$ is methyl, ethyl, i-propyl, i-butyl, tert-butyl, and cyclopropyl;

$N(R^7)_2$ is amino, or methylamino;

X is —$CH_2OH$,

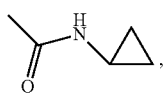

$C(O)NHCH_3$, or —$C(O)NHCH_2CH_3$;

or a pharmaceutically acceptable salt thereof.

Additional specific values include compounds wherein: the ring comprising $R^4$, $R^5$ and the atom to which they are connected is 2-methyl cyclohexane, 2,2-dimethylcyclohexane, 2-phenylcyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-cyclohexanecarboxylic acid, 4-cyclohexanecarboxylic acid esters, 4-methyloxyalkanoyl-cyclohexane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-carboxylic acid tert-butyl ester, tert-butylester, 1-piperidine-4-carboxylic acid methyl ester, or 1-piperidine-4-carboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, or 1-piperidine-3-carboxylic acid tert-butyl ester; or a pharmaceutically acceptable salt thereof.

Additional specific values include compounds having the formula (Ia), wherein:

$R^1$ is hydrogen or OH;

$R^2$ is hydrogen;

$R^3$ is hydrogen or OH;

the ring $CR^4R^5$ or $NR^4R^5$ is selected from the group consisting of:

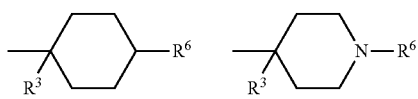

$R^6$ is —$CO_2R^a$;

$R^a$ is $(C_1-C_8)$alkoxy, $(C_3-C_6)$cycloalkyl, $(C_3-C_6)$cycloalkyl-$(C_1-C_3)$alkylene, heterocycle, and heterocycle-$(C_1-C_3)$alkylene;

wherein any of the alkyl, cycloalkyl, heterocycle, aryl, or heteroaryl groups of $R^a$, $R^b$ and $R^c$ is optionally substituted on carbon with 1 or 2 substituents selected from the group consisting of halo, $OR^e$, $(C_1-C_4)$alkyl, —CN, $NO_2$, trifluoromethyl, trifluoromethoxy, $CO_2R^3$, $NR^eR^e$, and $C(O)NR^eR^e$; and, $R^e$ is independently selected from H and $(C_1-C_4)$alkyl.

Exemplary compounds from that are expected to be useful in the present invention are shown in Table A below.

TABLE A

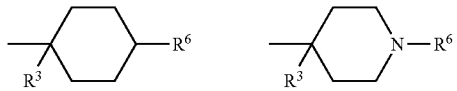

| Ex. # | $R^c$ | $R^7$ | —$(R^1)_m$—Z |
|---|---|---|---|
| 1. | Et | H | ![cyclohexane-COOMe with CH2*] |
| 2. | Et | H | ![piperidine-N-COOMe with CH2*] |
| 3. | cPr | H | ![piperidine-N-COOMe with CH2*] |
| 4. | Et | H | ![piperidine-N-COOEt with CH2*] |
| 5. | cPr | H | ![piperidine-N-COOEt with CH2*] |
| 6. | Et | H | ![piperidine-N-COO-iBu with CH2*] |

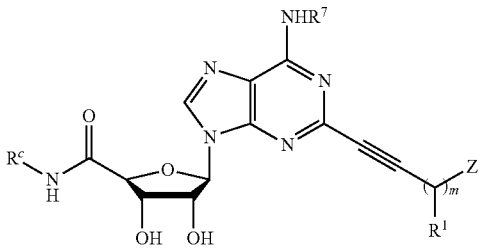
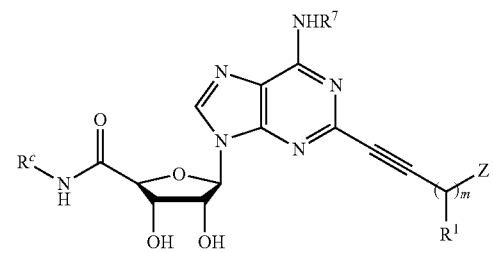

TABLE A-continued

| Ex. # | R$^c$ | R$^7$ | —(R$^1$)$_m$—Z |
|---|---|---|---|
| 21. | cPr | H | piperidine-N-C(O)O-cyclobutyl, 4-CH$_2$* |
| 22. | Et | H | piperidine-N-C(O)O-cyclobutyl, 4-CH$_2$* |
| 23. | Et | H | cyclohexyl-C(O)O-isopropyl, 4-CH$_2$* |
| 24. | cPr | H | cyclohexyl-C(O)O-methyl, 4-CH$_2$* |
| 25. | Et | H | cyclohexyl-C(O)-pyrrolidine, 4-CH$_2$* |
| 26. | Et | H | 3-methylcyclohexyl* (OH) |
| 27. | Et | H | 4-ethylcyclohexyl* (OH) |

TABLE A-continued

| Ex. # | R$^c$ | R$^7$ | —(R$^1$)$_m$—Z |
|---|---|---|---|
| 28. | Et | H | 3-methylcyclohexyl* (OH) |
| 29. | Et | H | 2-methylcyclohexyl* (OH) |
| 30. | Et | H | 4,4-dimethylcyclohexyl* (OH) |
| 31. | cPr | H | 3-methylcyclohexyl* (OH) |
| 32. | Et | H | 4-phenylcyclohexyl* (OH) |
| 33. | Et | H | norbornyl* (OH) |
| 34. | cPr | H | norbornyl* (OH) |

TABLE A-continued

Structure (Ex. 35-40):

| Ex. # | R$^c$ | R$^7$ | —(R$^1$)$_m$—Z |
|---|---|---|---|
| 35. | cPr | H | bornyl-OH group |
| 36. | Et | H | 2-adamantyl-OH |
| 37. | cPr | H | 2-adamantyl-OH |
| 38. | Et | H | decahydronaphthyl with HO and CH$_2$ |
| 39. | cPr | H | CH$_2$-piperidine-N-C(O)O-phenyl |
| 40. | Et | H | CH$_2$-piperidine-N-C(O)O-phenyl |

TABLE A-continued

| Ex. # | R$^c$ | R$^7$ | —(R$^1$)$_m$—Z |
|---|---|---|---|
| 41. | cPr | H | CH$_2$-piperidine-N-C(O)O-benzyl |
| 42. | Et | H | CH$_2$-piperidine-N-C(O)O-benzyl |

* signifies the point of attachment.

Further examples of agonists of A$_{2A}$ adenosine receptors that are expected to useful in the practice of the present invention include compounds having the formula II or a stereoisomer or pharmaceutically acceptable salt thereof:

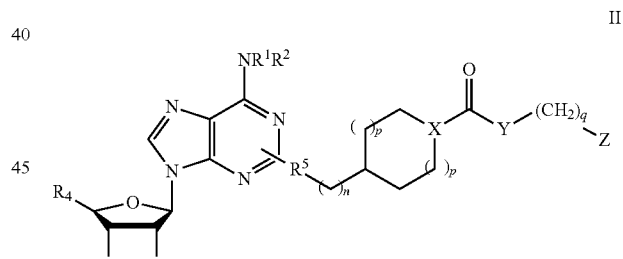

II wherein:

R$^1$ and R$^2$ independently are selected from the group consisting of H, (C$_1$-C$_8$)alkyl, (C$_3$-C$_8$)cycloalkyl, (C$_3$-C$_8$)cycloalkyl(C$_1$-C$_8$)alkylene, aryl, aryl(C$_1$-C$_8$)alkylene, heteroaryl, heteroaryl(C$_1$-C$_8$)alkylene-, diaryl(C$_1$-C$_8$)alkylene, and diheteroaryl(C$_1$-C$_8$)alkylene, wherein the aryl and heteroaryl rings are optionally substituted with 1-4 groups independently selected from fluoro, chloro, iodo, bromo, methyl, trifluoromethyl, and methoxy;

each R independently is selected from the group consisting of H, C$_1$-C$_4$ alkyl, cyclopropyl, cyclobutyl, and (CH$_2$)$_a$cyclopropyl;

X is CH or N, provided that when X is CH then Z cannot be substituted with halogen, C$_1$-C$_6$ alkyl, hydroxyl, amino, or mono- or di-(C$_1$-C$_6$-alkyl)amino;

Y is selected from the group consisting of O, $NR^1$, —$(OCH_2CH_2O)_mCH_2$—, and —$(NR^1CH_2CH_2O)_mCH_2$—, provided that when Y is O or $NR^1$, then at least one substituent is present on Z;

Z is selected from the group consisting of 5-membered heteroaryl, 6-membered aryl, 6-membered heteroaryl, carbocyclic biaryl, and heterocyclic biaryl, wherein the point of attachment of Y to Z is a carbon atom on Z, wherein Z is substituted with 0-4 groups independently selected from the group consisting of F, Cl, Br, I, ($C_1$-$C_4$)alkyl, —$(CH_2)_aOR^3$, —$(CH_2)_aNR^3R^3$, —NHOH, —$NR^3NR^3R^3$, nitro, —$(CH_2)_a$ CN, —$(CH_2)_aCO_2R^3$, —$(CH_2)_aCONR^3R^3$, trifluoromethyl, and trifluoromethoxy;

alternatively, Y and Z together form an indolyl, indolinyl, isoindolinyl, tetrahydroisoquinolinyl, or tetrahydroquinolinyl moiety wherein the point of attachment is via the ring nitrogen and wherein said indolyl, indolinyl, isoindolinyl, tetrahydroisoquinolinyl, or tetrahydroquinolinyl moiety, which is substituted with 0-4 groups independently selected from the group consisting of F, Cl, Br, I, $C_1$-$C_4$ alkyl, —$(CH_2)_aOR^3$, —$(CH_2)_aNR^3R^3$, —NHOH, —$NR^3NR^3R^3$, $NO_2$, —$(CH_2)_aCN$, —$(CH_2)_aCO_2R^3$, —$(CH_2)_aCONR^3R^3$, $CF_3$, and $OCF_3$;

$R^3$ is independently selected from the group consisting of H, ($C_1$-$C_6$)alkyl, cycloalkyl, aryl, and heteroaryl;

$R^4$ is selected from the group consisting of $CH_2OR$, C(O) NRR, and $CO_2R$;

$R^5$ is selected from the group consisting of $CH_2CH_2$, CH=CH, and C≡C;

a is selected from 0, 1, and 2;

m is selected from 1, 2, and 3;

n is selected from 0, 1, and 2;

each p independently is selected from 0, 1, and 2; and, q is selected from 0, 1, and 2.

Additional specific values include compounds having the formula IIa or a pharmaceutically acceptable salt thereof:

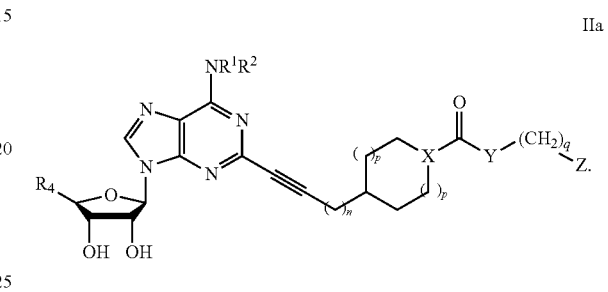

IIa

Additional specific values include compounds having the formula IIb or a pharmaceutically acceptable salt thereof:

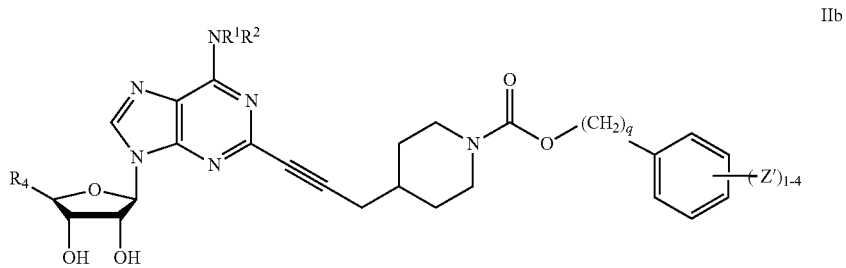

IIb wherein:

each Z' is independently selected from the group consisting F, Cl, Br, I, $C_1$-$C_4$ alkyl, —$(CH_2)_aOR^3$, —$(CH_2)_aNR^3R^3$, —NHOH, —$NR^3NR^3R^3$, $NO_2$, —$(CH_2)_aCN$, —$(CH_2)_a$ $CO_2R^3$, —$(CH_2)_aCONR^3R^3$, $CF_3$, and $OCF_3$.

Additional specific values include compounds wherein R is selected from H, methyl, ethyl or cyclopropyl.

Additional specific values include compounds having the formula IIc or a pharmaceutically acceptable salt thereof:

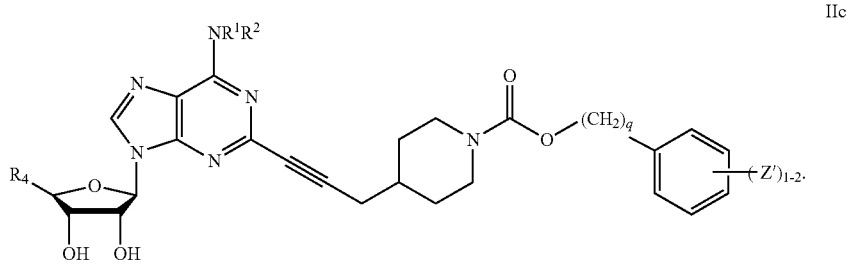

IIc

Additional specific values include compounds wherein Z' is selected from the group consisting of F, Cl, methyl, $OR^3$, $NO_2$, CN, $NR^3R^3$ and $CO_2R^3$.

Additional specific values include compounds wherein $R^3$ is methyl or hydrogen.

Additional exemplary compounds that are expected to be useful in the present invention are shown in Table B below.

TABLE B

| Ex. # | $R^4$ | Z' |
|---|---|---|
| 1 | C |  |
| 2 | C |  |
| 3 | C |  |
| 4 | A |  |
| 5 | C |  |
| 6 | A |  |
| 7 | A |  |
| 8 | C |  |
| 9 | C |  |
| 10 | C |  |
| 11 | A |  |
| 12 | A |  |
| 13 | A |  |
| 14 | C |  |
| 15 | B |  |
| 16 | B |  |
| 17 | C |  |
| 18 | C |  |
| 19 | B |  |
| 20 | C |  |
| 21 | C |  |
| 22 | C |  |
| 23 | C |  |

TABLE B-continued

| Ex. # | R⁴ | Z' |
|---|---|---|
| 24 | B | 2-fluorophenyl |
| 25 | B | 3-(methoxycarbonyl)phenyl |
| 26 | B | 2-chlorophenyl |
| 27 | A | 2-chlorophenyl |
| 28 | A | 2-methoxyphenyl |
| 29 | A | 4-methylphenyl |
| 30 | A | 4-nitrophenyl |
| 31 | B | 3-chlorophenyl |
| 32 | B | phenyl |
| 33 | B | 4-nitrophenyl |
| 34 | B | 2-aminophenyl |
| 35 | A | 3-chlorophenyl |
| 36 | A | 2-methoxyphenyl |
| 37 (iii) | B | 2-(hydroxyamino)phenyl |
| 38 (iii) | C | phenyl |
| 39 (iii) | C | 4-methylphenyl |
| 40 (iii) | C | 2-aminophenyl |
| 41 (iii) | C | 4-fluorophenyl |
| 42 | C | 2-chlorophenyl |
| 43 (ii) | C | 3-chlorophenyl |
| 44 (ii) | A | 4-fluorophenyl |
| 45 (ii) | A | 2-chlorophenyl |
| 46 (ii) | A | 3-chlorophenyl |
| 47 (ii) | C | 2,3-dimethylphenyl |
| 48 (ii) | C | 4-aminophenyl |

TABLE B-continued

| Ex. # | R⁴ | Z' |
|---|---|---|
| 49 | B | 2,3-dichlorophenyl |
| 50 | B | 2,3-difluorophenyl |
| 51 | C | 2,3-dichlorophenyl |
| 52 | C | 2,3-difluorophenyl |
| 53 | A | 2,3-dimethylphenyl |
| 54 | A | 2,3-difluorophenyl |
| 55 | A | 2,3-dichlorophenyl |
| 56 | C | 3-nitrophenyl |
| 57 | C | 3,5-dibromophenyl |

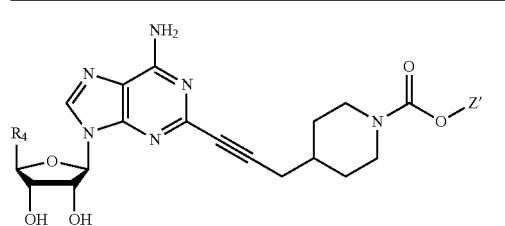

i

TABLE B-continued

| Ex. # | R⁴ | Z' |
|---|---|---| ii iii $R^4$ = A: $CH_2OH$; B: C(O)NEthyl; C: C(O)NCyclopropyl.

Compounds are of formula (i), unless indicated.

Additional specific values include compounds having the formula (Ib)-(Id) or a pharmaceutically acceptable salt thereof:

(Ib)

(Ic)

(Id)

Additional examples of $A_{2A}$ adenosine receptor agonists that are expected to be useful in the present invention include compounds of formula 4:

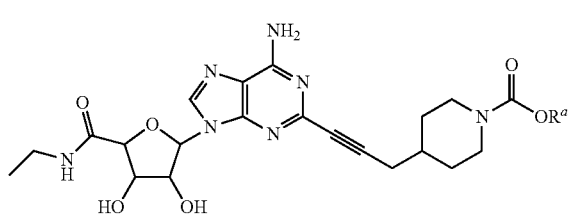

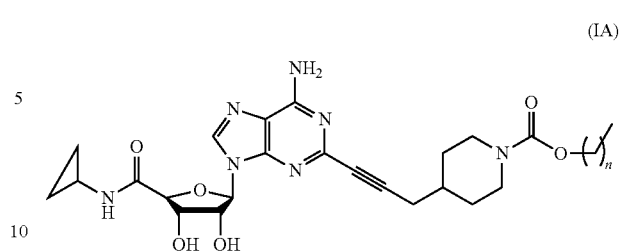

wherein $R^a$ is methyl, ethyl, propyl, isopropyl, isobutyl, or t-butyl.

Additional examples of $A_{2A}$ adenosine receptor agonists that are expected to be useful in the present invention include those described in U.S. Pat. No. 6,232,297 and in U.S. Patent Application No. 2003/0186926 A1.

Further examples of compounds expected to be useful in the present invention include formula (IA)

In formula (IA) n is 0, 1, 2, 3, 4, 5, 6, 7, 8, 9, 10, 11, 12, 13, 14, 15, 16, 17, or 18. In another group of specific compounds n is, 5, 6, 7, 8, 9, 10, 11, 12, 13, 14, 15, 16, 17, or 18.

Additional examples of $A_{2A}$ adenosine receptor agonists that are expected to be useful in the present invention include compounds of the invention include formula (IB)

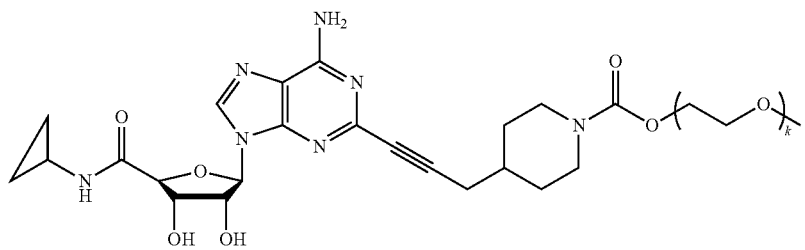

In formula (IB) k is 1, 2, 3, 4, 5, 6, 7, 8, 9, 10, 11, 12, 13, 14, 15, 16, 17, or 18.

Additional examples of $A_{2A}$ adenosine receptor agonists that are expected to be useful in the present invention include compounds of the invention include formula (IC)

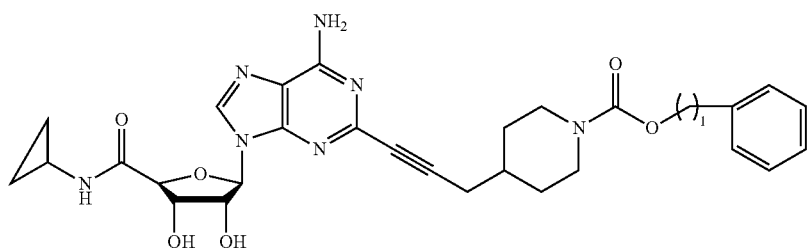

wherein l is 0, 1, 2, 3, or 4.

Other specific compounds of the invention include

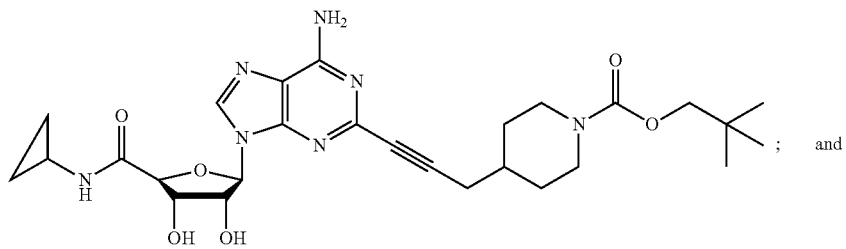

; and

-continued

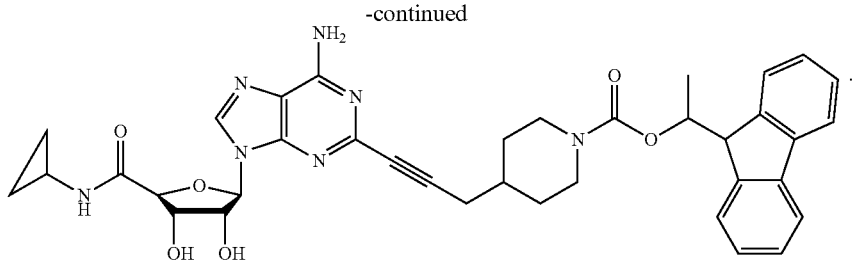

Additional examples of compounds expected to useful in the present invention are illustrated in tables 1, 2, and 3 below:

TABLE 1

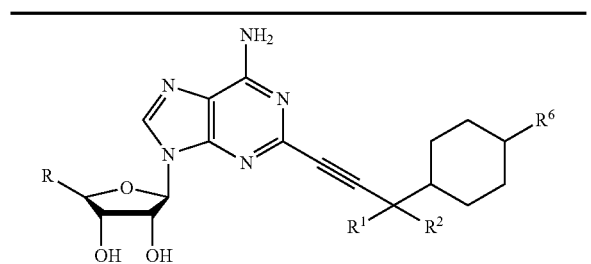

| Compound | R | $R^1$ | $R^2$ | $R^6$ |
|---|---|---|---|---|
| ATL2037 | NECA | H | H | $CH_2OH$ |
| MP9056 | NECA | OH | H | $CH_2OH$ |
| ATL146a | NECA | H | H | $CO_2H$ |
| MP9057 | NECA | OH | H | $CO_2H$ |
| ATL146e | NECA | H | H | $CO_2Me$ |
| MP9058 | NECA | OH | H | $CO_2Me$ |
| JR2145 | $CH_2OH$ | H | H | $CO_2Me$ |
| MP9059 | $CH_2OH$ | OH | H | $CO_2Me$ |
| ATL193 | NECA | H | H | $CH_2OAc$ |
| MP9060 | NECA | OH | H | $CH_2OAc$ |
| JR2147 | $CH_2OH$ | H | H | $CH_2OAc$ |
| MP9061 | $CH_2OH$ | OH | H | $CH_2OAc$ |
| JR3023 | NECA | H | H | $CH_2N(CH_3)_2$ |
| MP9062 | NECA | OH | H | $CH_2N(CH_3)_2$ |
| JR3021 | NECA | H | H | $COOCH_2CH_2NHBoc$ |
| MP9063 | NECA | OH | H | $COOCH_2CH_2NHBoc$ |
| JR3033 | NECA | H | H | $COOCH_2CH_2NH_2$ |
| MP9064 | NECA | OH | H | $COOCH_2CH_2NH_2$ |
| JR3037 | NECA | H | H | $CONHCH_2CH_3$ |
| MP9065 | NECA | OH | H | $CONHCH_2CH_3$ |
| JR3055 | NECA | H | H | $CONH_2$ |
| MP9072 | NECA | OH | H | $CONH_2$ |
| JR3065 | NECA | H | H | CONHMe |
| MP9066 | NECA | OH | H | CONHMe |
| JR3067B | NECA | H | H | Me, cis $CO_2Me$ |
| MP9067 | NECA | OH | H | Me, cis $CO_2Me$ |
| JR3067A | NECA | H | H | Me, trans $CO_2Me$ |
| MP9068 | NECA | OH | H | Me, trans $CO_2Me$ |
| JR3087 | NECA | H | H | $CH_2CH_3$ |
| MP9069 | NECA | OH | H | $CH_2CH_3$ |
| JR3159A | NECA | OH | H | H |
| JR3159B | NECA | OH | H | H |
| JR3119 | NECA | H | H | $COCH_3$ |
| MP9070 | NECA | OH | H | $COCH_3$ |
| JR3121 | NECA | H | H | $CHCH_3(OH)$ |
| MP9071 | NECA | OH | H | $CHCH_3(OH)$ |
| JR3139 | NECA | OH | $C_6H_{11}$ | H |

NECA = $CH_3CH_2N(H)C(O)$—

TABLE 2

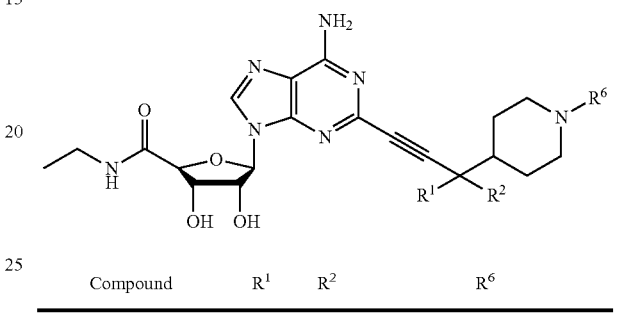

| Compound | $R^1$ | $R^2$ | $R^6$ |
|---|---|---|---|
| JR3261 | H | H | H |
| JR3259 | H | H | $CO_2tBu$ |
| JR3269 | H | H | $CO_2Et$ |
| JR4011 | H | H | $CO_2iBu$ |
| JR4009 | H | H | $CO_2iPr$ |
| JR4007 | H | H | COMe |
| JR4051 | H | H | $COC(CH_3)_3$ |
| JR4047 | H | H | $COCH_2(CH_3)_3$ |
| MP9047 | H | H | $COCH_3$ |
| MP9048 | H | H | $C(O)N(CH_3)_2$ |
| MP9049 | H | H | $C(O)N(CH_3)Et$ |
| MP9050 | H | H | $C(O)N(CH_3)iPr$ |
| MP9051 | H | H | $C(O)N(CH_3)iBu$ |
| MP9052 | H | H | $C(O)NH(CH_3)$ |
| MP9053 | H | H | $C(O)NH(Et)$ |
| MP9054 | H | H | $C(O)NH(iPr)$ |
| MP9055 | H | H | $C(O)NH(iBu)$ |
| TX3261 | OH | H | H |
| TX3259 | OH | H | $CO_2tBu$ |
| TX3269 | OH | H | $CO_2Et$ |
| TX4011 | OH | H | $CO_2iBu$ |
| TX4009 | OH | H | $CO_2iPr$ |
| TX4007 | OH | H | COMe |
| TX4051 | OH | H | $COC(CH_3)_3$ |
| TX4047 | OH | H | $COCH_2(CH_3)_3$ |
| TX9047 | OH | H | $COCH_3$ |
| TX9048 | OH | H | $C(O)N(CH_3)_2$ |
| TX9049 | OH | H | $C(O)N(CH_3)Et$ |
| TX9050 | OH | H | $C(O)N(CH_3)iPr$ |
| TX9051 | OH | H | $C(O)N(CH_3)iBu$ |
| TX9052 | OH | H | $C(O)NH(CH_3)$ |
| TX9053 | OH | H | $C(O)NH(Et)$ |
| TX9054 | OH | H | $C(O)NH(iPr)$ |
| TX9055 | OH | H | $C(O)NH(iBu)$ |

TABLE 3

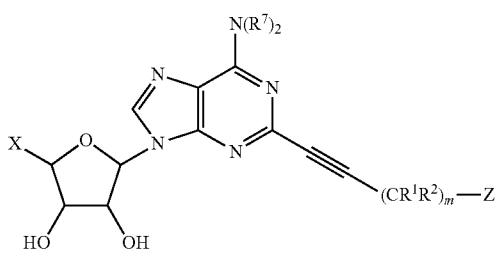

| Compound | n | $R^3$ | $R^6$ |
|---|---|---|---|
| JR3135 | 1 | OH | H |
| JR3089 | 2 | OH | H |
| JR3205 | 2 | $NH_2$ | H |
| JR3177A | 2 | OH | 2-$CH_3$ |
| JR3177B | 2 | OH | 2-$CH_3$ |
| JR3181A | 2 | OH | 2-$CH_3$ |
| JR3181B | 2 | OH | 2-$CH_3$ |
| JR3227 | 2 | OH | 2-$C(CH_3)_3$ |
| JR9876 | 2 | OH | 2-$C_6H_5$ |
| JR3179 | 2 | OH | 3-$CH_3$ |
| JR3221 | 2 | OH (R) | 3-$CH_3$ (R) |
| ATL 203 | 2 | OH (S) | 3-$CH_3$ (R) |
| MP9041 | 2 | OH (R) | 3-$CH_3$ (S) |
| MP9042 | 2 | OH (S) | 3-$CH_3$ (S) |
| JR3201B | 2 | OH | 3-$(CH_3)_2$ |
| MP9043 | 2 | OH (R) | 3-$CH_2CH_3$ (R) |
| MP9044 | 2 | OH (S) | 3-$CH_2CH_3$ (R) |
| MP9045 | 2 | OH (R) | 3-$CH_2CH_3$ (S) |
| MP9046 | 2 | OH (S) | 3-$CH_2CH_3$ (S) |
| JR3163 | 2 | OH | 3-$(CH_3)_2$, 5-$(CH_3)_2$ |
| JR9875 | 2 | OH | 4-$CH_3$ |
| JR3149 | 2 | OH | 4-$C_2H_5$ |
| JR3203 | 2 | OH | 4-$C(CH_3)_3$ |
| JR3161 | 2 | OH | 4-$C_6H_5$ |

Additional examples of $A_{2A}$ adenosine receptor agonists that are expected to be useful in the present invention include compounds of formula (II):

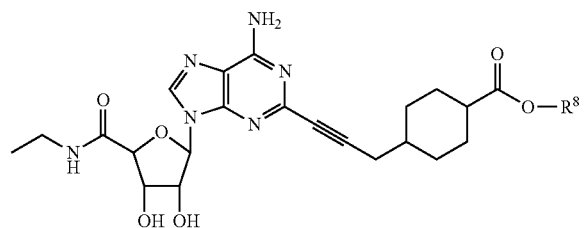

(II)

wherein Z is $CR^3R^4R^5$; each $R^1$, $R^2$ and $R^3$ is hydrogen; $R^4$ and $R^5$ together with the carbon atom to which they are attached form a cycloalkyl ring having 3, 4, 5, 6, 7, 8, 9 or 10 ring atoms; and wherein the ring comprising $R^4$ and $R^5$ is substituted with —$(CH_2)_{0-6}$—Y; where Y is —$CH_2OR^a$, —$CO_2R^a$, —$OC(O)R^a$, —$CH_2OC(O)R^a$, —$C(O)NR^bR^c$, —$CH_2SR^a$, —$C(S)OR^a$, —$OC(S)R^a$, —$CH_2OC(S)R^a$ or $C(S)NR^bR^c$ or —$CH_2N(R^b)(R^c)$;

each $R^7$ is independently hydrogen, $(C_1-C_8)$alkyl, $(C_3-C_8)$ cycloalkyl, aryl or aryl$(C_1-C_8)$alkylene;

X is —$CH_2OR^a$, —$CO_2R^a$, —$CH_2OC(O)R^a$, —$C(O)NR^bR^c$, —$CH_2SR^a$, —$C(S)OR^a$, —$CH_2OC(S)R^a$, $C(S)NR^bR^c$ or —$CH_2N(R^b)(R^c)$;

each $R^a$, $R^b$ and $R^c$ is independently hydrogen, $(C_1-C_8)$ alkyl, or $(C_1-C_8)$alkyl substituted with 1-3 $(C_1-C_8)$alkoxy, $(C_3-C_8)$cycloalkyl, $(C_1-C_8)$alkylthio, amino acid, aryl, aryl $(C_1-C_8)$alkylene, heteroaryl, or heteroaryl$(C_1-C_8)$alkylene; or $R^b$ and $R^c$, together with the nitrogen to which they are attached, form a pyrrolidino, piperidino, morpholino, or thiomorpholino ring; and m is 0 to about 6; or a pharmaceutically acceptable salt thereof.

A specific value for —$N(R^7)_2$ is amino, monomethylamino or cyclopropylamino.

A specific value for Z is carboxy- or —$(C_1-C_4)$alkoxycarbonyl-cyclohexyl$(C_1-C_4)$alkyl.

A specific value for $R^a$ is H or $(C_1-C_4)$alkyl, i.e., methyl or ethyl.

A specific value for $R^b$ is H, methyl or phenyl.

A specific value for $R^c$ is H, methyl or phenyl.

A specific value for —$(CR^1R^2)_m$— is —$CH_2$— or —$CH_2$—$CH_2$—.

A specific value for X is $CO_2R^a$, $(C_2-C_5)$alkanoylmethyl or amido.

A specific value for Y is $CO_2R^a$, $(C_2-C_5)$alkanoylmethyl or amido.

A specific value for m is 1.

Specific compounds expected to be useful for practicing the invention are compounds JR3259, JR3269, JR4011, JR4009, JR-1085 and JR4007.

Specific $A_{2A}$ adenosine receptor agonists expected to be useful in the present invention having formula (II) include those described in U.S. Pat. No. 6,232,297.

Specific compounds of formula (II) are those wherein each $R^7$ is H, X is ethylaminocarbonyl and Z is 4-carboxycyclohexylmethyl (DWH-146a), Z is 4-methoxycarbonylcyclohexylmethyl (DWH-146e), Z is 4-isopropylcarbonylcyclohexylmethyl (AB-1), Z is 4-acetoxymethylcyclohexylmethyl (JMR-193) or Z is 4-pyrrolidine-1-carbonylcyclohexylmethyl (AB-3).

Additional examples of $A_{2A}$ adenosine receptor agonists that are expected to be useful in the present invention include those depicted below.

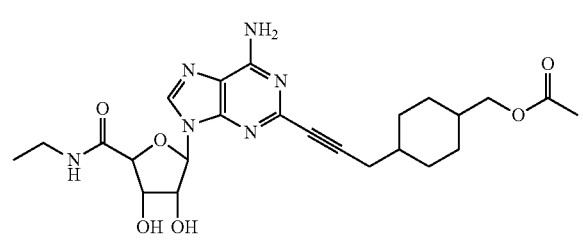

DWH-146: $R^8$ = H or Me.
AB-1: $R^8$ = iPr

JMR-193

AB-3

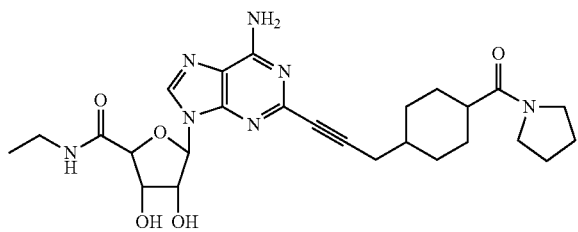

JR-1085

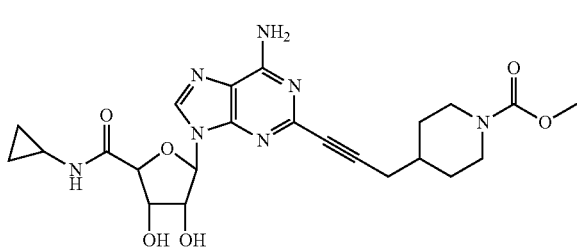

Additional examples of $A_{2A}$ adenosine receptor agonists of formula (II) that are expected to be useful in the present invention include those described in U.S. Pat. No. 6,232,297. These compounds, having formula (II), can be prepared according to the methods described therein.

Another specific group of agonists of $A_{2A}$ adenosine receptors that are expected to be useful in the practice of the present invention include compounds having the general formula (III):

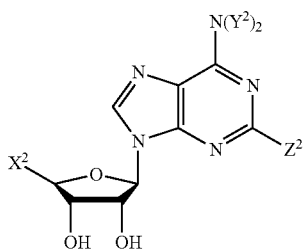

(III)

wherein $Z^2$ is a group selected from the group consisting of —$OR^{12}$, —$NR^{13}R^{14}$, a —C̃C—$Z^3$, and —NH—N=$R^{17}$;

each $Y^2$ is individually H, $C_1$-$C_6$ alkyl, $C_3$-$C_7$ cycloalkyl, phenyl or phenyl $C_1$-$C_3$ alkyl;

$R^{12}$ is $C_{1-4}$-alkyl; $C_{1-4}$-alkyl substituted with one or more $C_{1-4}$-alkoxy groups, halogens (fluorine, chlorine or bromine), hydroxy groups, amino groups, mono($C_{1-4}$-alkyl)amino groups, di($C_{1-4}$-alkyl)amino groups or $C_{6-10}$-aryl groups wherein the aryl groups may be substituted with one or more halogens (fluorine, chlorine or bromine), $C_{1-4}$-alkyl groups, hydroxy groups, amino groups, mono($C_{1-4}$-alkyl)amino groups or di($C_{1-4}$-alkyl)amino groups); or $C_{6-10}$-aryl; or $C_{6-10}$-aryl substituted with one or more halogens (fluorine, chlorine or bromine), hydroxy groups, amino groups, mono ($C_{1-4}$-alkyl)amino groups, di($C_{1-4}$-alkyl)amino groups or $C_{1-4}$-alkyl groups;

one of $R^{13}$ and $R^{14}$ has the same meaning as $R^{12}$ and the other is hydrogen; and $R^{17}$ is a group having the formula (i)

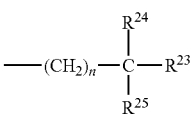

(i)

wherein each of $R^{15}$ and $R^{16}$ independently may be hydrogen, ($C_3$-$C_7$)cycloalkyl or any of the meanings of $R^{12}$, provided that $R^{15}$ and $R^{16}$ are not both hydrogen;

$X^2$ is $CH_2OH$, $CH_3$, $CO_2R^{20}$ or C(=O)$NR^{21}R^{22}$ wherein $R^{20}$ has the same meaning as $R^{13}$ and wherein $R^{21}$ and $R^{22}$ have the same meanings as $R^{15}$ and $R^{16}$ or $R^{21}$ and $R^{22}$ are both H;

$Z^3$ has one of the following meanings:

$C_6$-$C_{10}$ aryl, optionally substituted with one to three halogen atoms, $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino $C_1$-$C_3$ monoalkylamino, $C_2$-$C_6$ dialkylamino, methylenedioxy or aminocarbonyl;

a group of formula —$(CH_2)_q$—Het wherein q is 0 or an integer from 1 to 3 and Het is 5 or 6 membered heterocyclic aromatic or non-aromatic ring, optionally benzocondensed, containing 1 to 3 heteroatoms selected from non-peroxide oxygen, nitrogen or sulphur, linked through a carbon atom or through a nitrogen atom;

$C_3$-$C_7$ cycloalkyl optionally containing unsaturation or $C_2$-$C_4$ alkenyl;

(ii)

wherein
$R^{23}$ is hydrogen, methyl or phenyl;
$R^{24}$ is hydrogen, $C_1$-$C_6$ linear or branched alkyl, $C_5$-$C_6$ cycloalkyl or $C_3$-$C_7$ cycloalkenyl, phenyl-$C_1$-$C_2$-alkyl or $R^{23}$ and $R^{24}$, taken together, form a 5 or 6-membered carbocyclic ring or $R^{25}$ is hydrogen and $R^{23}$ and $R^{24}$, taken together, form an oxo group or a corresponding acetalic derivative;
$R^{25}$ is OH, $NH_2$ dialkylamino, halogen, cyano; and n is 0 or 1 to 4; or $C_1$-$C_{16}$ alkyl, optionally comprising 1-2 double bonds, O, S or $NY^2$;
or a pharmaceutically acceptable salt thereof.

Specific $C_{6-10}$-aryl groups include phenyl and naphthyl.

Additional specific values include compounds wherein in the compound of formula (III), $Z^2$ is a group of the formula (iii)

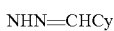

(iii)

wherein n is an integer from 1-4, e.g., 2, and Ar is a phenyl group, tolyl group, naphthyl group, xylyl group or mesityl group. In one embodiment, Ar is a para-tolyl group and n=2.

Additional specific values include compounds wherein in the compound of formula (III), $Z^2$ is a group of the formula (iv)

NHN=CHCy          (iv)

wherein Cy is a $C_{3-7}$-cycloalkyl group, such as cyclohexyl or a $C_{1-4}$ alkyl group, such as isopropyl.

Additional specific values include compounds wherein in the compound of formula (III), $Z^2$ is a group of the formula (vii)

$$C\equiv CZ^3 \quad (v)$$

wherein $Z^3$ is $C_3$-$C_{16}$ alkyl, hydroxy $C_2$-$C_6$ alkyl or (phenyl)(hydroxymethyl).

Additional examples of compounds of formula (III) include those shown below:

WRC-0470

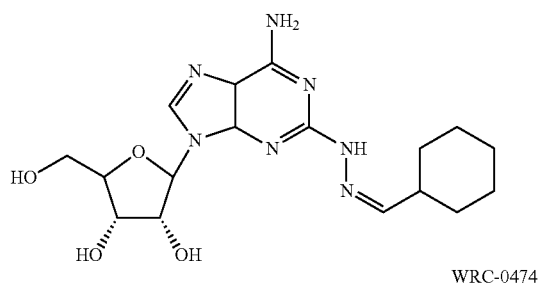
WRC-0474

WRC-0090

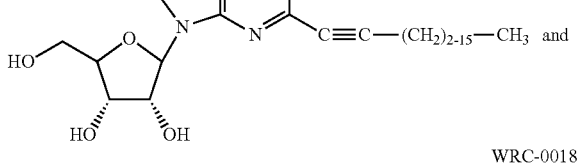

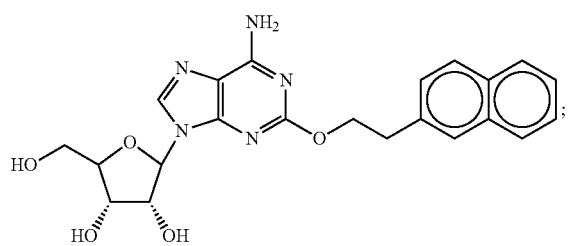
WRC-0018

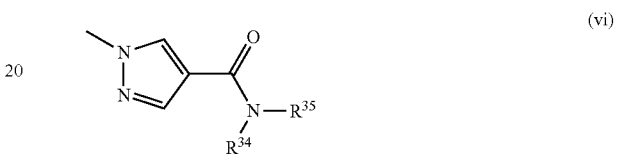

wherein the H on $CH_2OH$ can optionally be replaced by ethylaminocarbonyl. Of these specific examples, WRC-0474 [SHA 211] and WRC-0470 are particularly preferred.

Such compounds may be synthesized as described in: Olsson et al. (U.S. Pat. Nos. 5,140,015 and 5,278,150); Cristalli (U.S. Pat. No. 5,593,975); Miyasaka et al. (U.S. Pat. No. 4,956,345); Hutchinson, A. J. et al., *J. Pharmacol. Exp. Ther.*, 251, 47 (1989); Olsson, R. A. et al., *J. Med. Chem.*, 29, 1683 (1986); Bridges, A. J. et al., *J. Med. Chem.*, 31, 1282 (1988); Hutchinson, A. J. et al., *J. Med. Chem.*, 33, 1919 (1990); Ukeeda, M. et al., *J. Med. Chem.*, 34, 1334 (1991); Francis, J. E. et al., *J. Med. Chem.*, 34, 2570 (1991); Yoneyama, F. et al., *Eur. J. Pharmacol.*, 213, 199-204 (1992); Peet, N. P. et al., *J. Med. Chem.*, 35, 3263 (1992); and Cristalli, G. et al., *J. Med. Chem.*, 35, 2363 (1992); all of which are incorporated herein by reference.

Additional specific values include compounds having formula (III) where $Z^2$ is a group having formula (vi):

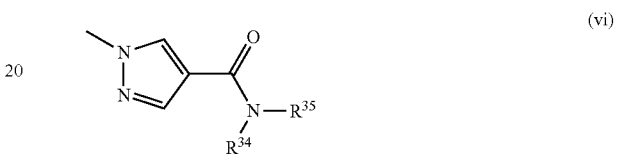
(vi)

wherein $R^{34}$ and $R^{35}$ are independently H, $C_1$-$C_6$ alkyl, $C_3$-$C_7$ cycloalkyl, phenyl, phenyl $C_1$-$C_3$ alkyl or $R^{34}$ and $R^{35}$ taken together with the nitrogen atom are a 5- or 6-membered heterocyclic ring containing 1-2 heteroatoms selected from non-peroxide oxygen, nitrogen ($N(R^{13})$) or sulphur atoms. In one embodiment, one of $R^{34}$ and $R^{35}$ is hydrogen and the other is ethyl, methyl or propyl. In another embodiment, one of $R^{34}$ and $R^{35}$ is hydrogen and the other is ethyl or methyl.

A specific pyrazole derivative that is expected to be useful in practicing the present invention is a compound having the formula:

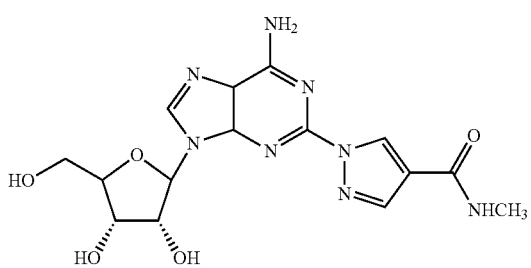 [SMILES: CNC(=O)c1cnn(C2=NC3C(N=CN3C3OC(CO)[C@@H](O)[C@H]3O)C(N)=N2)c1]

Another specific group of agonists of $A_{2A}$ adenosine receptors that are expected to be useful in the present invention include compounds having the general formula (IV):

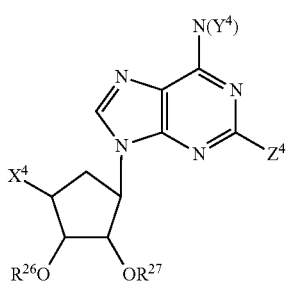
(IV)

wherein $Z^4$ is $-NR^{28}R^{29}$;

$R^{28}$ is hydrogen or $(C_1-C_4)$ alkyl; and $R^{29}$ is a) $(C_1-C_4)$alkyl;

b) $(C_1-C_4)$alkyl substituted with one or more $(C_1-C_4)$ alkoxy, halogen, hydroxy, amino, mono$((C_1-C_4)$alkyl)amino, di$((C_1-C_4)$alkyl)amino or $(C_6-C_{10})$aryl wherein aryl is optionally substituted with one or more halogen, hydroxy, amino, $(C_1-C_4)$alkyl, $R^{30}$OOC—$(C_1-C_4)$alkyl)-, $R^{31}R^{32}$NC($=$O)—($(C_1-C_4)$alkyl)-, mono$((C_1-C_4)$alkyl)amino or di$((C_1-C_4)$alkyl)amino;

c) $(C_6-C_{10})$aryl; or d) $(C_6-C_{10})$aryl substituted with one or more halogen, hydroxy, amino, mono$((C_1-C_4)$alkyl)amino, di$((C_1-C_4)$alkyl)amino or $(C_1-C_4)$alkyl;

wherein each $Y^4$ is individually H, $(C_1-C_6)$alkyl, $(C_3-C_7)$cycloalkyl, phenyl or phenyl$(C_1-C_3)$alkyl; and $X^4$ is $-C(=O)NR^{31}R^{32}$, $-COOR^{30}$, or $-CH_2OR^{30}$;

wherein each of $R^{31}$ and $R^{32}$ are independently; hydrogen; $C_{3-7}$-cycloalkyl; $(C_1-C_4)$alkyl; $(C_1-C_4)$alkyl substituted with one or more $(C_1-C_4)$alkoxy, halogen, hydroxy, $-COOR^{33}$, amino, mono$((C_1-C_4)$alkyl)amino, di$((C_1-C_4)$alkyl)amino or $(C_6-C_{10})$aryl wherein aryl is optionally substituted with one or more halogen, $(C_1-C_4)$alkyl, hydroxy, amino, mono$((C_1-C_4)$alkyl)amino or di$((C_1-C_4)$alkyl)amino; $(C_6-C_{10})$aryl; or $(C_6-C_{10})$aryl substituted with one or more halogen, hydroxy, amino, mono$((C_1-C_4)$alkyl)amino, di$((C_1-C_4)$alkyl)amino or $(C_1-C_4)$alkyl;

$R^{26}$ and $R^{27}$ independently represent hydrogen, lower alkanoyl, lower alkoxy-lower alkanoyl, aroyl, carbamoyl or mono- or di-lower alkylcarbamoyl; and $R^{30}$ and $R^{33}$ are independently hydrogen, $(C_1-C_4)$alkyl, $(C_6-C_{10})$aryl or $(C_6-C_{10})$aryl$((C_1-C_4)$alkyl); or a pharmaceutically acceptable salt thereof.

Additional specific values include compounds wherein at least one of $R^{28}$ and $R^{29}$ is $(C_1-C_4)$alkyl substituted with one or more $(C_1-C_4)$alkoxy, halogen, hydroxy, amino, mono$((C_1-C_4)$alkyl)amino, di$((C_1-C_4)$alkyl)amino or $(C_6-C_{10})$aryl wherein aryl is optionally substituted with one or more halogen, hydroxy, amino, $(C_1-C_4)$alkyl, $R^{30}$OOC—$(C_1-C_4)$alkyl, mono$((C_1-C_4)$alkyl)amino or di$((C_1-C_4)$alkyl)amino.

Additional specific values include compounds wherein at least one of $R^{31}$ and $R^{32}$ is $C_{1-4}$-alkyl substituted with one or more $(C_1-C_4)$alkoxy, halogen, hydroxy, amino, mono$((C_1-C_4)$alkyl)amino, di$((C_1-C_4)$alkyl)amino or $C_{6-10}$-aryl wherein aryl is optionally substituted with one or more halogen, hydroxy, amino, $(C_1-C_4)$alkyl, $R^{30}$OOC—$(C_1-C_4)$alkylene-, mono$((C_1-C_4)$alkyl)amino or di$((C_1-C_4)$alkyl)amino.

Additional specific values include compounds wherein at least one of $R^{28}$ and $R^{29}$ is $C_{6-10}$-aryl substituted with one or more halogen, hydroxy, amino, mono$((C_1-C_4)$alkyl)amino, di$((C_1-C_4)$alkyl)amino or $(C_1-C_4)$alkyl.

Additional specific values include compounds wherein at least one of $R^{31}$ and $R^{32}$ is $C_{6-10}$-aryl substituted with one or more halogen, hydroxy, amino, mono$((C_1-C_4)$alkyl)-amino, di$((C_1-C_4)$alkyl)amino or $(C_1-C_4)$alkyl.

Additional specific values include compounds wherein $R^{31}$ is hydrogen and $R^{32}$ is $(C_1-C_4)$alkyl, cyclopropyl or hydroxy-$(C_2-C_4)$alkyl. A specific $R^{28}$ group is $(C_1-C_4)$alkyl substituted with $(C_6-C_{10})$aryl, that is in turn substituted with $R^{30}$O(O)C—$(C_1-C_4)$alkylene-.

A specific compound having formula (IV) is:

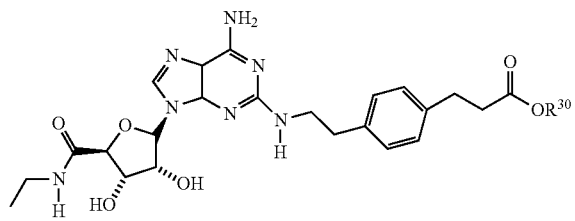

wherein $R^{30}$ is hydrogen, methyl, ethyl, n-propyl or iso-propyl. One embodiment provides a compound wherein the $R^{30}$ group is methyl or ethyl. In one embodiment, the $R^{30}$ group is methyl.

Two compounds that can be used in practicing the present invention have the formula:

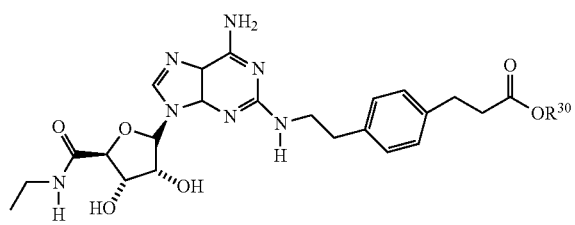

wherein $R^{30}$ is hydrogen (acid, CGS21680) and where $R^{30}$ is methyl (ester, JR2171).

The compounds of the invention having formula (IV) may be synthesized as described in: U.S. Pat. No. 4,968,697 or *J. Med. Chem.*, 33, 1919-1924, (1990).

Another agonist compound expected to be useful in the present invention is IB-MECA:

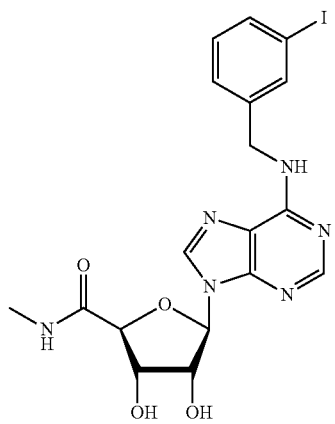

It will be appreciated by those skilled in the art that the compounds of formulas described herein, e.g., (I), (II), (III), and (IV), have more than one chiral center and may be isolated in optically active and racemic forms. In one embodiment, the riboside moiety of the compounds is derived from D-ribose, i.e., the 3□, 4□-hydroxyl groups are alpha to the sugar ring and the 2□ and 5□ groups is beta (3R, 4S, 2R, 5S). When the two groups on the cyclohexyl group are in the 1- and 4-position, they are preferably trans. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

It is understood that any embodiment or feature of the present invention whether characterized as preferred or not characterized as preferred may be combined with any other embodiment or feature of the invention, whether such other feature is characterized as preferred or not characterized as preferred.

Definitions

The following definitions are used, unless otherwise described.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

$A_{2A}$ agonist refers to an agent that agonizes the Adenosine $A_{2A}$ receptor with a Ki of <1 μM. An $A_{2A}$ agonist may be selective for $A_{2A}$ (e.g., at least 10, 50, or 100/1 over another adenosine receptor subtype/$A_{2A}$ receptor). An $A_{2A}$ agonist may also be cross reactive with other adenosine receptor subtypes (e.g., $A_1$, $A_{2B}$, and $A_3$). The $A_{2A}$ agonist may activate other receptors with a greater or lesser affinity than the $A_{2A}$ receptor.

It will be appreciated by those skilled in the art that compounds of the invention having a chiral center may exist in and be isolated in optically active, and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein; it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine therapeutic activity using the standard tests described herein or using other similar tests which are well known in the art.

Examples of the molecular weight of compounds useful in the present invention can include (a) less than about 500, 550, 600, 650, 700, 750, 800, 850, 900, 950, or 1000 grams per mole; (b) less than about 950 grams per mole; (c) less than about 850 grams per mole, and, (d) less than about 750 grams per mole.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

Stable means that the compound is suitable for pharmaceutical use.

The present invention covers stable compound and thus avoids, unless otherwise specified, the following bond types: heteroatom-halogen, N—S, O—S, O—O, and S—S.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, i-butyl, s-butyl, t-butyl, n-pentyl, and s-pentyl.

"Haloalkyl" includes both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl.

"Hydroxyalkyl" includes both branched and straight-chain saturated aliphatic hydrocarbon groups having the specified number of carbon atoms, substituted with 1 or more hydroxy groups (e.g., 1, 2, or 3 OH). Examples of hydroxyl alkyl include hydroxymethyl, hydroxyethyl, and hydroxy-n-propyl.

"Alkoxy" is an alkyl-O-group.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups. Cycloalkyl also include bicycloalkyl and tricycloalkyl, both of which include fused and bridged rings (e.g., norbornane and adamantane).

"Halo" or "halogen" refers to fluoro, chloro, bromo, and iodo.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Mammal and patient covers warm blooded mammals that are typically under medical care (e.g., humans and domesticated animals). Examples of mammals include (a) feline, canine, equine, bovine, and human and (b) human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to a indication listed herein. "Therapeutically effective amount" also includes an amount of the combination of compounds claimed that is effective to treat the desired indication. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Specific and preferred values listed for radicals, substituents, and ranges, are for illustration only; they do not exclude other defined values or other values within defined ranges for the radicals and substituents.

The preparation of compounds useful in practicing the present invention are described in numerous patents and published application, including U.S. Pat. No. 6,232,297; USAN 2003/0186926; USAN 2006/0217343; USAN 2006/0040888; and, USAN 2006/0040889.

The following abbreviations have been used herein:
2-Aas 2-alkynyladenosines;
ATL146e 4-{3-[6-Amino-9-(5-ethylcarbamoyl-3,4-dihydroxy-tetrahydro-furan-2-yl)-9H-purin-2-yl]-prop-2-ynyl}cyclohexanecarboxylic acid methyl ester;
ATL313 4-{3-[6-Amino-9-(5-cyclopropylcarbamoyl-3,4-dihydroxy-tetrahydro-furan-2-yl)-9H-purin-2-yl]-prop-2-ynyl}-piperidine-1-carboxylic Acid methyl ester (Example 2 of USAN 2006/0040888);
CGS21680 2-[4-(2-carboxyethyl)phenethylamino]-5'-N-ethyl-carboxamidoadenosine;
Cl-IB-MECA N6-3-iodo-2-chlorobenzyladenosine-5'-N-methyluronamide;
NECA 5'-N-ethylcarboxamidoadenosine;
IB-MECA N6-3-iodobenzyladenosine-5'-N-methyluronamide,
2-Iodoadenosine 5-(6-amino-2-iodo-purin-9-yl)-3,4-dihydroxytetra-hydro-furan-2-carboxylic acid ethylamide
INECA 2-iodo-N-ethylcarboxamidoadenosine
MRS 1220, N-(9-chloro-2-furan-2-yl-[1,2,4]triazolo[1,5-c]quinazolin-5-yl)-2-phenylacetamide;
NECA N-ethylcarboxamidoadenosine The compounds of the present invention can be formulated as pharmaceutical compositions and administered to a mammalian host, such as a human patient in a variety of forms adapted to the chosen route of administration, e.g., orally or parenterally, by intravenous, intramuscular, topical, inhalation or subcutaneous routes. Exemplary pharmaceutical compositions are disclosed in "Remington: The Science and Practice of Pharmacy", A. Gennaro, ed., 20th edition, Lippincott, Williams & Wilkins, Philadelphia, Pa.

Thus, the present compounds may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from (a) about 0.1-25 wt % and (b) about 0.5-10 wt %. The concentration in a semi-solid or solid composition such as a gel or a powder will be (a) about 0.1-5 wt % and (b) about 0.5-2.5 wt %.

The amount of the compound or an active salt or derivative thereof, required for use in treatment will vary not only with the particular compound or salt selected but also with the route of administration, the nature of the condition being treated, and the age and condition of the patient and will be ultimately at the discretion of the attendant physician or clinician. In general, however, a suitable dose will be in the range of from (a) about 1.0-100 mg/kg of body weight per day, (b) about 10-75 mg/kg of body weight per day, and (c) about 5-20 mg per kilogram body weight per day.

The compound can be conveniently administered in unit dosage form; e.g., tablets, caplets, etc., containing (a) about 4-400 mg, (b) about 10-200 mg, and (c) about 20-100 mg of active ingredient per unit dosage form.

Ideally, the active ingredient should be administered to achieve peak plasma concentrations of the active compound of from (a) about 0.02-20 µM, (b) about 0.1-10 µM, and (c) about 0.5-5 µM. These concentrations may be achieved, for example, by the intravenous injection of a 0.005-0.5% solution of the active ingredient, or orally administered as a bolus containing about 4-400 mg of the active ingredient.

The compounds of the invention can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention.

EXAMPLES

A mouse model has been enabled in which selective temporary occlusion of blood flow into the left liver lobe results in a profound acceleration of tumor growth in the clamped liver lobes, but not in the unclamped liver lobes. An $A_{2A}$ receptor agonist was then studied to determine its effect on the accelerated tumor growth.

Detailed Protocol

1. Before the Experiment: Animals

Male Balb/C mice (10-12 weeks) are housed under standard laboratory conditions with free access to water and chow and a 12-hour dark-light cycle.

2. Before the Experiment: Cell Culture

The murine colon carcinoma cell line C26 is cultured in Dulbecco's modified Eagle's medium supplemented with 5% heat-inactivated fetal calf serum, penicillin (100 units/ml) and streptomycin (100 µg/ml) in a 5% carbon dioxide environment.

3. Day 0: Induction of Liver Metastases

Confluent cultures of the C26 cell line are harvested by brief trypsinization (0.05 trypsin in 0.02% EDTA).

After centrifugation, single cell suspensions are prepared in PBS to a final concentration of $5 \times 10^4$ cells/100 µl.

Cell viability is determined by trypan blue staining, and should be ≥98%.

The induction of liver metastases is performed under inhalation anesthesia with a 1.5-2% isoflurane/O2 mixture using a mask.

Buprenorfine (3 µg/mouse) is administered intramuscularly prior to surgery to provide sufficient intra- and postoperative analgesia.

Surgical procedures are performed under aseptic conditions.

Body temperature is maintained at 36.5-37.5° C. by placing the animals on a heated table and covering them by aluminium foil.

Through a left lateral flank incision, $5 \times 10^4$ C26 colorectal carcinoma cells are injected into the splenic parenchyma (within an hour after trypsinisation).

After ten minutes, the spleen is removed to prevent intrasplenic tumor growth.

After the procedure a small amount of saline is left in the abdominal cavity and the peritoneum and skin are separately closed with 5.0 vicryl.

Animals are allowed to recover from anesthesia under standard laboratory conditions and are allowed free access to water and chow.
4. Day 0-5:
Micrometastases are allowed to develop throughout the liver for 5 days.
5. Day 5: Marine Model of Hepatic I/R
The induction of hepatic I/R is performed under inhalation anesthesia with a 1.5-2% isoflurane/O2 mixture using a mask.
Buprenorfine (3 μg/mouse) is administered intramuscularly prior to surgery to provide sufficient intra- and postoperative analgesia.
Surgical procedures are performed under aseptic conditions.
Body temperature is maintained at 36.5-37.5° C. by placing the animals on a heated table and covering them by aluminium foil.
ATL-313 solutions are prepared and suspended in osmotic minipumps (Alzet) at a dose of 3 ng/kg/min. Minipumps are placed in normal saline at 37° C. for at least 4 hours prior to the operation, to allow immediate drug delivery.
After laparotomy, mice receive an intraperitoneal bolus injection of 1 ng/kg ATL-313.
A control group received the $A_{2A}R$ antagonist ZM241385 as an intraoperative bolus (1 micro-g/kg) and subsequently continuously using osmotic intraperitoneal minipumps (10 ng/kg/min; 3 days).
Sham operated mice undergo laparotomy with exposure of the liver but without interruption of hepatic flow.
Partial hepatic I/R is induced by occluding the vascular inflow of the left lateral liver lobe for 45 minutes, corresponding to approximately 40% of the liver mass.
Surgical foil is placed over the laparotomy wound to avoid dehydration.
After removal of the clamps a small amount of saline is left in the abdominal cavity
The peritoneum and skin are separately closed with 5.0 vicryl.
6. Day 5-10:
Micrometastases are allowed to grow out to macrometastases (approximately 10-20% of the non-clamped lobes at day 10) for 5 days
7. Day 10:
Livers were harvested, fixed in formalin, and embedded in paraffin. Tissue sections were stained with H&E and the following parameters were assessed by an operator who was blinded to treatment.
1. Hepatic Replacement Area: =morphometric assessment of the % liver tissue that has been replaced by tumor tissue
HRA ratios=ratio between HRA values in the ischemic (clamped) versus the non-ischemic lobes.
Necrosis=morphometric assessment of % liver tissue that has become necrotic.
HRA and necrosis values were assessed on 4 non-sequential H&E-stained tissue sections by semi-automated stereology (Leica Q-Prodit system, Leica Microsystems, Rijswijk, The Netherlands) using a 4-points grid overlaid on 100 fields per slide at a magnification of 40×.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating liver tumor micrometastases following liver resection, comprising:
administering to a patient experiencing liver metastases a therapeutically effective amount of an $A_{2A}$ adenosine receptor agonist of formula 1 or 2 or a stereoisomer or pharmaceutically acceptable salt thereof:

2. The method of claim 1, wherein the $A_{2A}$ adenosine receptor agonist is a compound of the following formula or a pharmaceutically acceptable salt thereof:

3. The method of claim 1, wherein the $A_{2A}$ adenosine receptor agonist is a compound of the following formula or a pharmaceutically acceptable salt thereof:

4. The method of claim 1, wherein the agonist is administered prior to liver resection.
5. The method of claim 1, wherein the agonist is administered during liver resection.
6. The method of claim 1, wherein the agonist is administered post liver resection.
7. The method of claim 1, wherein the agonist is administered prior to and post liver resection.

* * * * *